United States Patent [19]
Prutchi et al.

[11] Patent Number: 5,701,895
[45] Date of Patent: Dec. 30, 1997

[54] SUBCUTANEOUS ELECTRICAL DATA PORT

[75] Inventors: David Prutchi, Lake Jackson; Roy Simmons, III, Houston, both of Tex.

[73] Assignee: Sulzer Intermedics Inc., Angleton, Tex.

[21] Appl. No.: 726,550

[22] Filed: Oct. 7, 1996

Related U.S. Application Data

[63] Continuation of Ser. No. 557,688, Nov. 13, 1995, abandoned.

[51] Int. Cl.$^6$ ....................................................... A61B 5/00
[52] U.S. Cl. ......................................... 128/630; 128/899
[58] Field of Search ................................... 128/901, 630, 128/899; 607/1, 2, 9, 27, 30–33, 36–38, 60, 61, 52

[56] References Cited

U.S. PATENT DOCUMENTS

| | | |
|---|---|---|
| 3,959,772 | 5/1976 | Wakasa et al. . |
| 4,146,029 | 3/1979 | Ellinwood, Jr. . |
| 4,774,951 | 10/1988 | Osypka ........................... 607/36 |
| 4,823,600 | 4/1989 | Biegel et al. . |
| 4,890,497 | 1/1990 | Cahill . |
| 5,205,286 | 4/1993 | Soukup et al. ..................... 128/630 |
| 5,358,514 | 10/1994 | Schulman et al. ................... 607/61 |

FOREIGN PATENT DOCUMENTS

| | | | |
|---|---|---|---|
| 2568477 | 2/1986 | France | ............... 607/33 |

*Primary Examiner*—William E. Kamm
*Assistant Examiner*—George R. Evanisko
*Attorney, Agent, or Firm*—John R. Merkling

[57] ABSTRACT

An implantable subcutaneous data port for transferring data received from a sensor implanted within a subject. The data port electrically connects to the sensor and includes a control circuit electrically connected to an access port. The control circuit includes a current loop transmitter which modulates a current loop signal with voltage outputs from the sensor. This current loop signal transmits through the access port to an externally located current loop receiver which converts the current loop signal into an output voltage. Needle electrodes are insertable through the skin of the subject to the access port and provide an electrical interface between the control circuit and current loop receiver.

10 Claims, 5 Drawing Sheets

SUBCUTANEOUS ELECTRICAL DATA PORT

This application is a continuation of application Ser. No. 08/577,688 filed on Nov. 13, 1995 abandoned.

BACKGROUND

Development of medical devices, drugs, and treatments depends on accurately retrieving clinical data from a subject under investigation. Data collecting and sensing devices provide one way to retrieve these data. These device often include sensors or electrodes which must be implanted within the subject in order to provide clinicians with access to the sensed information.

Retrieving data from implanted sensors poses a potential problem since data frequently must be retrieved on numerous different occasions and over an extended period of time. If surgery is required each time data is retrieved, the subject may be overly exposed to stress, trauma, or risk of infection. In order to develop and test cardiac pacemakers and defibrillators, for example, clinicians need to monitor electrical activity of the subject's head. One way to monitor this activity is to surgically implant one end of an electrode to the heart. The other end of the electrode may be left subcutaneously (i.e., under the skin) or transcutaneously (i.e., through the skin). In the former instance, access to the electrode may require an invasive procedure, such as surgery. In the latter instance, prolonged and chronic exposure of the electrode through the skin may cause discomfort, lead to infection, or cause damaging stress on the electrode.

Devices are now available which allow minimally invasive access to an implanted electrode or sensor. One such device is a data port. The data port is surgically implanted beneath the subject's skin and then electrically connected to the implanted lead or sensor. Access ports are located on the body of the data port and provide electrical access to the implanted lead or sensor. When electrical connection to an implanted electrode, for example, is required, a conductive needle is inserted through the subject's skin and into one of the access ports. The needle enters the access port and establishes electrical connection with the electrode. Trauma to the subject is minimized since the needle pierces the skin and surgery is not otherwise necessitated.

One disadvantage associated with the data ports and similar type devices concerns the reliability of information transmitted through the needle. In this regard, the needle does not provide a completely reliable contact with the access port. When the needle is connected to the access port, the impedance associated with this connection may vary widely and in a non-predictable manner if the subject moves. Even small movements of the skin near the point of insertion produce a sheering force against the needle. This movement, in turn, produces a variation in contact impedance between the needle and the access port. Variations in impedance tend to introduce noise and errors in measurements obtained from the implanted sensor or electrode. When clinicians are monitoring low-amplitude impedance signals, such as intercardiac conduction measurements, even relatively small movements of the needle may result in relatively large changes in resistance between the needle itself and the access port. This fluctuation of resistance induces large amounts of unwanted noise and artifacts to the sensed signal.

A chronic transcutaneous electrical connector is another device which allows minimally invasive access to an implanted electrode or sensor. This type of connector may be implanted such that part of the connector is permanently left to protrude through the skin. After the connector is implanted, the skin grows around the connector leaving a portion exposed to make external electrical connections. See for example Kenzo Akazawa, et al. "Functional Neuromuscular Stimulation System Using an Implantable Hydroxyapatite Connector and a Microprocessor-Based Portable Stimulator" *IEEE Transactions on Biomedical Engineering*, Vol. 36, No. 7, (1989), pp. 746–753.

One disadvantage associated with the chronic transcutaneous connectors concerns the risk of infection. Since the connector partially protrudes through the skin, debris and microorganisms tend to penetrate the skin and, in turn, expose the subject to serious and recurrent infections. Prolonged exposure of the connector through the skin also may be an irritant for the subject.

It therefore would be advantageous to provide an implantable data port which reliably transfers data and is not prone to introduce noise and errors during data transmission.

It also would be advantageous to provide a data port which offers minimally invasive access to data and is not prone to unwanted infections.

SUMMARY OF THE INVENTION

The present invention is addressed to an implantable subcutaneous data port which reliably transfers data and is not prone to acquire electrical noise during data transmission. The data port utilizes a current loop which is insensitive to noise and immune to errors from line impedance. In this regard, the data port electrically connects to a sensor which is implanted within the subject under investigation. This sensor may be located within or outside the data port and collects data from the subject. A control circuit is located within the data port and is electrically connected to the sensor for receiving sensor output. The control circuit includes a current loop transmitter which modulates a two-wire current loop signal with the sensor output. This current loop signal then transfers to an externally located electrical converter having a current loop receiver. This current loop receiver converts the current loop signal into an output voltage. Modulation of the current loop signal with the sensor output and conversion of the current loop signal back to an output voltage enables reliable data transfer from the data port to devices remotely located from the subject.

In the preferred embodiment, the data port and sensor are surgically implanted subcutaneously in the subject. Thereafter, needle electrodes may be inserted through the skin of the subject to access ports located on the data port. These access ports provide an electrical interface between the control circuit and the externally located electrical converter. The electrical converter includes a control loop receiver and a power source. The power source supplies power to the current loop transmitter. As such, signal transfer from the control circuit to the electrical converter is insensitive to resistance changes between the access port and needle electrodes when such resistance is between about zero to several hundred ohms. In addition, a portion of the loop current can be used to power the implanted current loop transmitter, sensor excitation, signal conditioning circuitry, and other implanted circuitry.

DETAILED DESCRIPTION OF THE INVENTION

Figure 1:
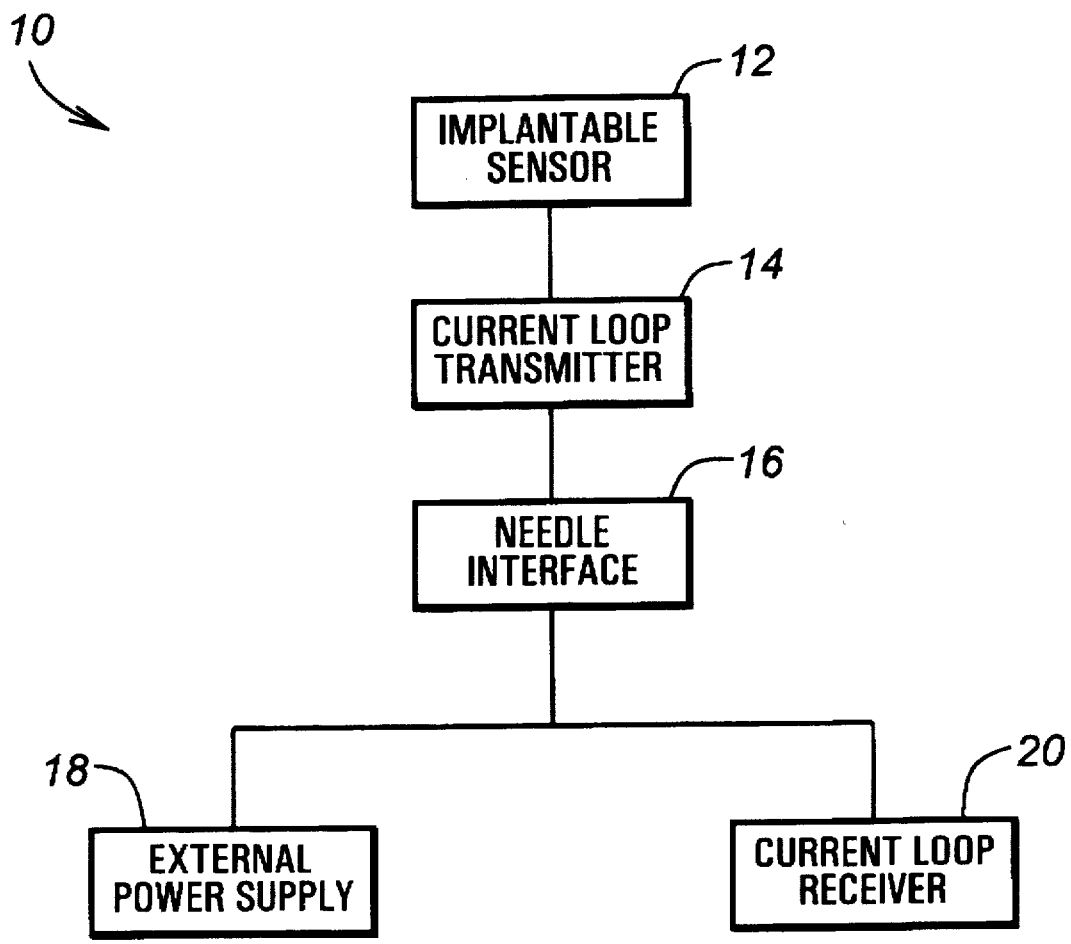
FIG. 1 is a block diagram of a system according to the invention.

FIG. 1 illustrates a block diagram of a system 10 according to the invention. System 10 generally is directed toward an implantable data port for reliably communicating signals from an implanted sensor to an external electrical device. Voltage sensor outputs communicate from the sensor to the data port. Thereafter, a current loop signal is modulated with the voltage sensor output, and this current loop signal then is transferred to an external electrical converter which re-converts the signal to an output voltage.

As shown, system 10 comprises an implantable sensor 12, a current loop transmitter 14, a needle interface 16, an external power supply 18, and a current loop receiver 20. Sensor 12 is subcutaneously implantable within a subject (not shown) and may be any of a variety of different sensing devices which sense information. The sensor, for example, may sense patient blood pressure, heart beat, blood oxygenation, ventilation, or the like. Sensor 12 also may be an electrode, such as an endocardial or epicardial cardiac electrode.

Current loop transmitter 14 electrically connects to sensor 12 and is subcutaneously implantable within the subject. Transmitter 14 modulates a current loop signal with voltage sensor output from sensor 12. This current loop signal then transmits through needle interface 16 to external power supply 18 and current loop receiver 20. Interface 16 provides a transcutaneous electrical connection between transmitter 14 and power supply 18 and current loop receiver 20.

Figure 2:
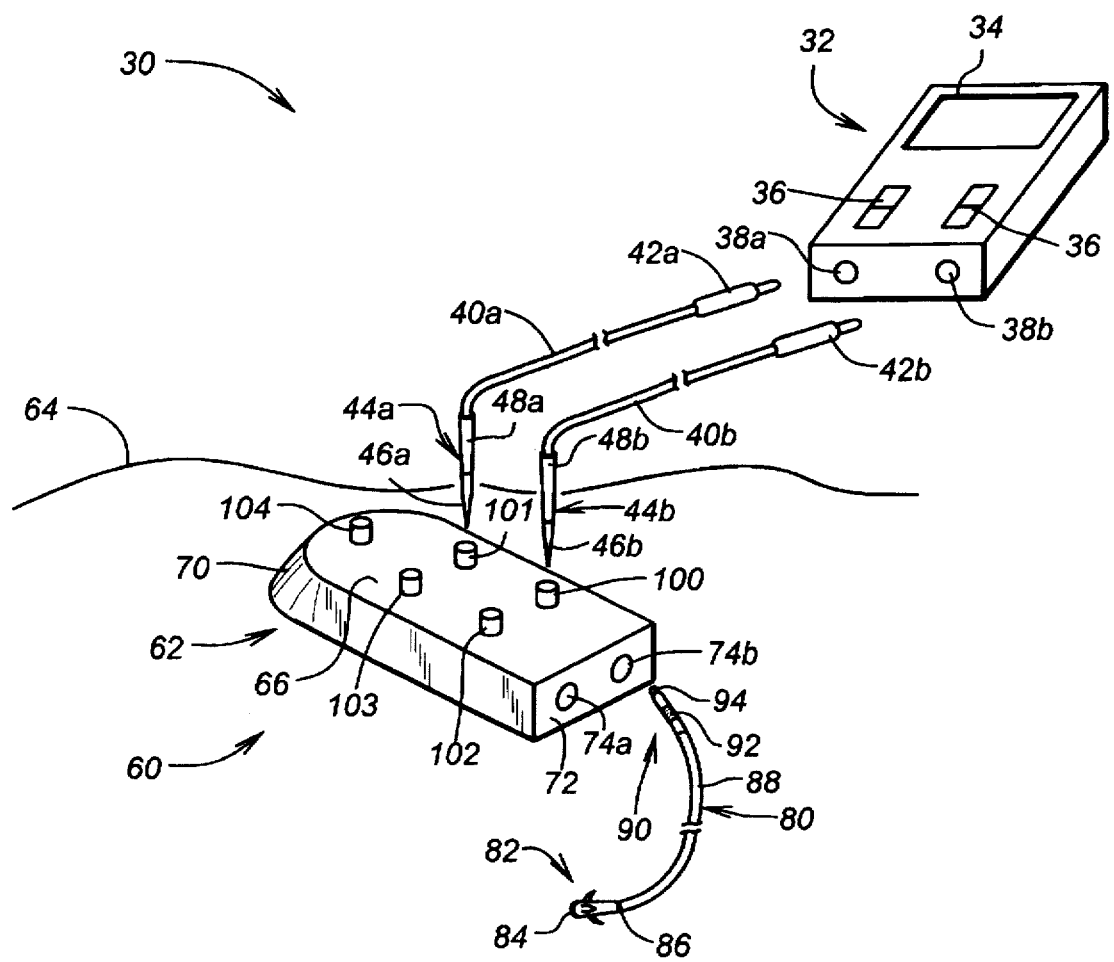
FIG. 2 is a perspective view of a data port according to the invention utilized in conjunction with peripheral devices.

Looking now to FIG. 2, an exemplary system according to the invention is shown generally at 30. An electrical converter 32 has a visual display 34, controls 36, and two female electrical connectors 38a and 38b. Converter 32 includes an electrical circuit (not shown) having a power supply and a current loop receiver.

Two needle electrodes 40a and 40b include a first end having a male electrical connector 42a and 42b, respectively. Each male connector 42a and 42b is connectable to one of female connectors 38a and 38b for establishing electrical contact. Each needle electrode 40a and 40b further includes a pointed end 44a and 44b, respectively, for penetrating the skin of the subject. Ends 44a and 44b have a conductive tip 46a and 46b and a shank 48a and 48b. Each electrically conductive shank has an electrically nonconductive outer surface which is coated with Teflon, for example. Additionally, ends 44a and 44b preferably are formed from a non-toxic, electrically conductive material.

Figure 3:
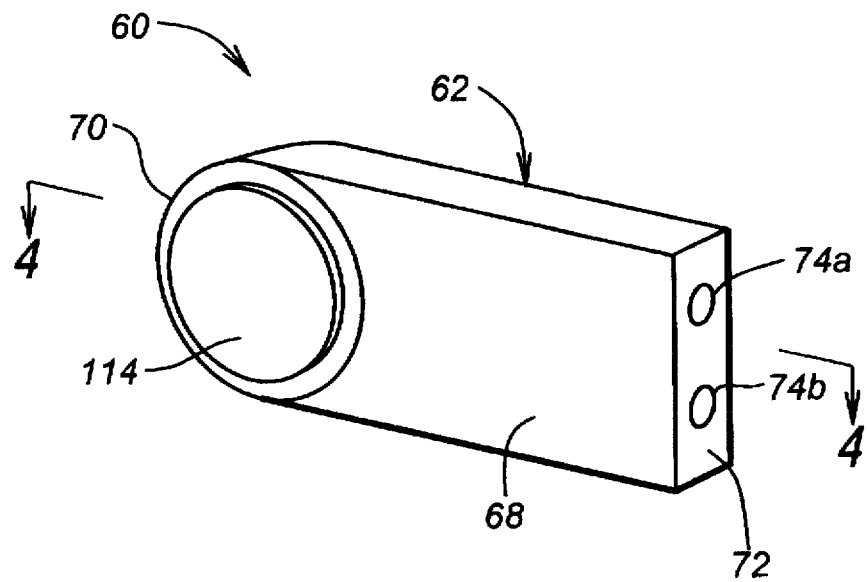
FIG. 3 is a perspective view of a data port.

A data port 60 is subcutaneously implantable within living subjects and includes a non conductive body 62 made of biologically compatible material. Preferably, body 62 has a hardened epoxy core (not shown) surrounded with silicone rubber. Body 62 may have a variety of configurations but, preferably, is flattened to fit subcutaneously right beneath the skin 64 of the subject. Turning also to FIG. 3, an upper surface 66 of body 62 will lie adjacent the underside of skin 64, and a lower surface 68 will lie against muscle or bone at an implant site. A first end 70 is semi-circular and rounded, and a second end 72 is flat. Two female connector ports 74a and 74b are located at end 72. Connector ports 74a and 74b are electrically connectable to a sensor 80. These connector ports may be provided, for example, as a standard SL-1 connector. Sensor 80 is shown as a bipolar endocardial lead which is commercially available and sold, for example, as model number 430-07 manufactured by Intermedics, Inc. In this regard, sensor 80 has a first passive fixation end 82 with two electrodes 84 and 86. Electrodes 84 and 86 extend within an insulated casing 88 to a male connector end 90 and establish electrical connection with one of the connector ports 74a and 74b through two electrical contacts 92 and 94. Connector end 90 may be a standard VS-1/IS-1 connector. A fluid tight seal forms when connector end 90 inserts into connector ports 74a and 74b.

Figure 4:
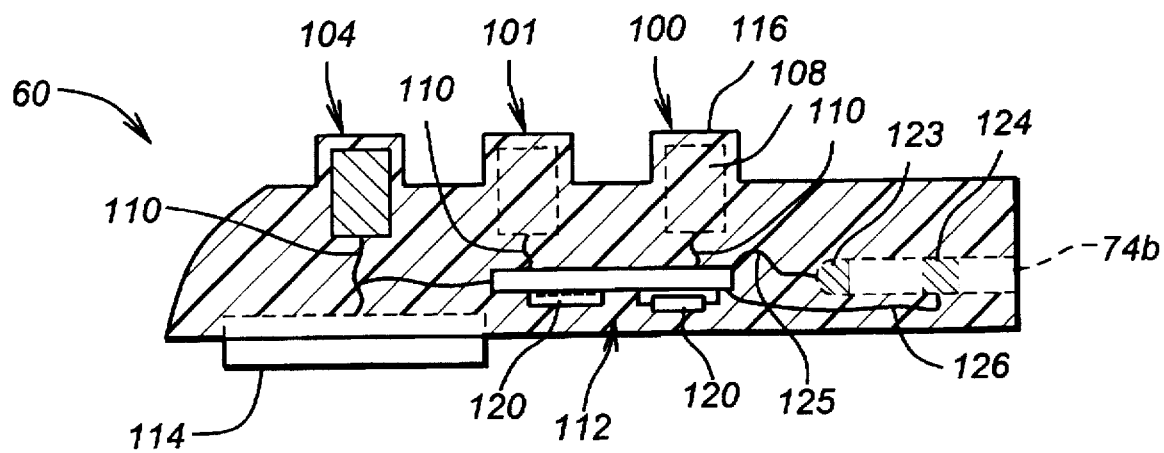
FIG. 4 is a sectional view taken through the line 4—4 of FIG. 3.

Body 62 has a plurality of access ports 100–104 extending from upper surface 66. Access ports 100–104 provide an electrical connection between needle electrodes 40a and 40b and data port 60 and are shown having a cylindrical configuration. Looking to FIG. 4, preferably, access ports 100–104 include a conductive filler 108 for providing electrical communication through the access ports. Conductive wires 110 provide electrical connection from filler 108. In this regard, access ports 100–103 are electrically connected to a control circuit 112, and access port 104 is electrically connected to a reference electrode 114. This reference electrode 114 provides a replicable ground or body reference electrode. Preferably, wires 110 have a low resistance and comprise, for example, silver DFT (drawn/filament/tube) or gold, silver DBS (drawn/brazed/stranded). A silicone cap 116 covers and seals each filler 108.

Control circuit 112 includes a plurality of circuit components, depicted generally at 120. As shown, connector port 74b electrically connects to control circuit 112. In this regard, port 74b includes electrodes 123 and 124 which connect to control circuit 112 via conductive wires 125 and 126, respectively. Connection between connector port 74a and control circuit 112 is similarly established.

Figure 5:
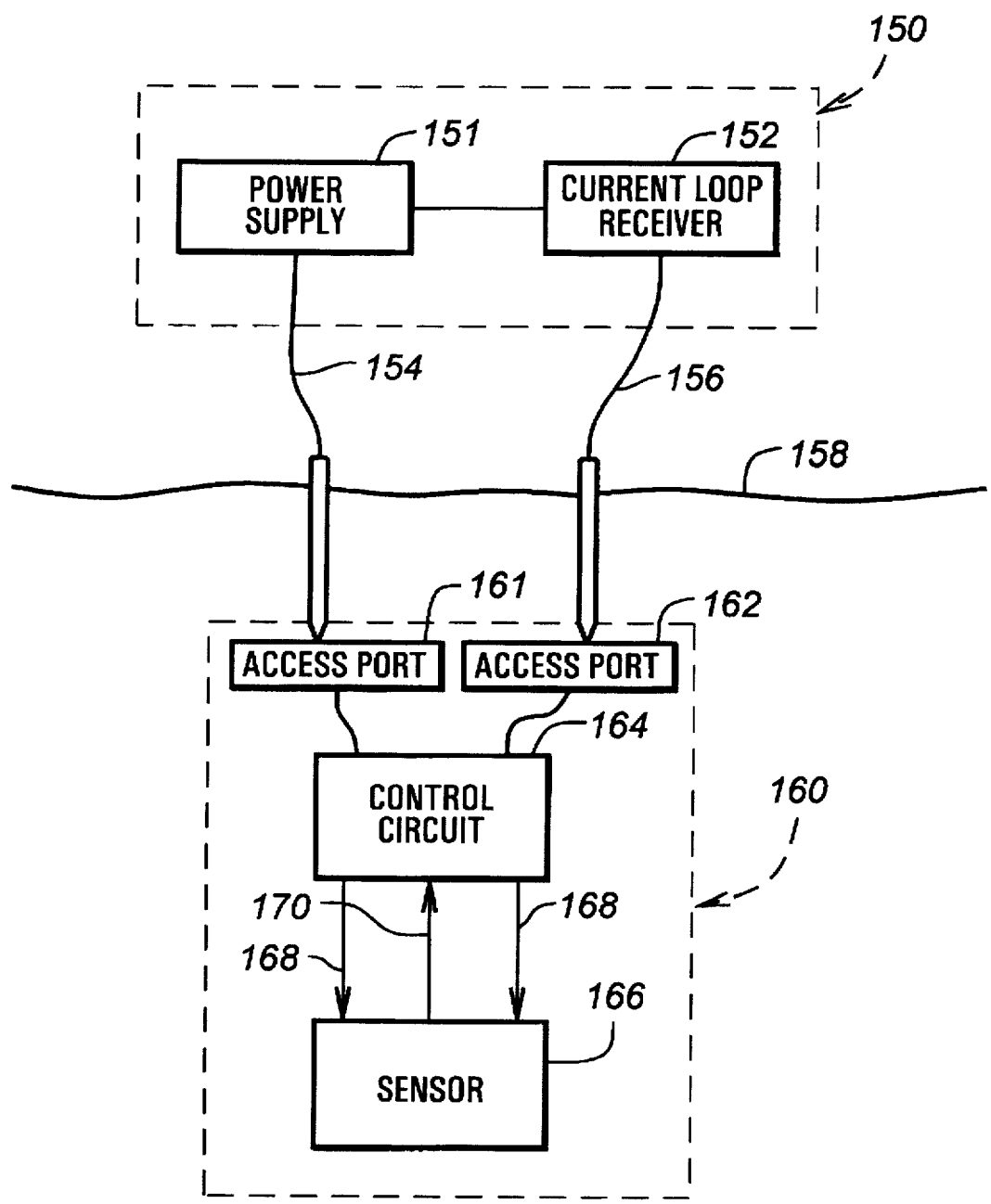
FIG. 5 is a block schematic of the circuitry of a system according to the invention.

An important feature of the present invention is the ability of the data port to reliably transmit signals to locations outside the subject. FIG. 5 presents a block schematic view of the circuitry of the present invention. Block 150 represents an electrical device having a power supply 151 and a current loop receiver 152. Power supply 151 electrically connects to needle electrode 154 and may have a variety of circuitry configurations from a d.c. battery to an a.c. to d.c. converter. Current loop receiver circuit 152 connects to needle electrode 156 and may have a variety of circuitry configurations from a resistive element to a more complex over-the-counter current loop receiver, such as the RCV420 manufactured by Burr-Brown which converts a 4–20 mA loop current to a 0 to 5 V output voltage.

Needle electrodes 154 and 156 are positionable through skin 158 of a subject (not shown) to implanted data port 160. Data port 160 includes access ports 161 and 162 in order to establish electrical connection between electrical device 150 and a control circuit 164. Access ports 161 and 162 preferably include areas of conductive filler, wire mesh, metallic filet, or other conductive type material. Regardless of the configuration or choice of materials, access ports 161 and 162 should provide an electrical interface for data port 160, and, in particular, establish electrical connections to control circuit 164.

Preferably, control circuit 164 includes a precision, low-drift two-wire current loop transmitter, such as the XTR101 manufactured by Burr-Brown. Control circuit 164 electrically connects to sensor 166 via electrical pathways shown at 168 and 170. Sensor 166 may include a variety of different types of sensing devices, such as the cardiac lead shown in FIG. 2. Sensor 166 may be disposed within data port 160 or, alternatively, located remotely from port 160 and electrically connected thereto. In this regard, for example, sensor 166 could be an electrode affixed to the heart of the subject. Additionally, pathways 168 may carry control and sensor excitation signals to sensor 166, for example, while pathway 170 carries sensor output signals back to control circuit 164.

In practice, data port 160 is positioned subcutaneously under skin 158 and is electrically connected to sensor 166. Skin 158 then is closed and allowed to heal. Thereafter, in order to establish an electrical connection with data port 160, the clinician will locate access ports 161 and 162. Preferably, access ports 161 and 162 are configured to allow the clinician to identify its location. Needle electrodes 154 and 156 are then electrically connected to electrical device 150. These electrodes are inserted through skin 158 and into access ports 161 and 162 to establish an electrical connection with data port 160. Power supply 151 causes a current flow through access ports 161 and 162 to control circuit 164. The control circuit modulates this current flow as function of a voltage from sensor 166. In particular, the control circuit ensures that the current flowing between its input through needle electrode 154 and its output through needle electrode 156 is proportional to the voltage output from sensor 166. Once the current flow is modulated, it then is directed back through access port 162 to electrical device 150. Current loop receiver 154 then reconverts the current flow to an output voltage. As such, the current flow from data port 160, and in particular from control circuit 164, is insensitive to resistance changes between needle electrodes 154 and 156 and access port 161 and 162.

Another feature of the present invention is that electrical contact between needle electrodes 154 and 156 and respective access port 161 and 162 remains insensitive to contact resistance variations within reasonable limitations. For example, if power supply 151 is 24 V and current loop receiver has a resistance of 75 ohms, then the total contact resistance between needle electrodes 154 and 156 and access port 161 and 162 will be in the zero to about a few hundred ohm range.

Figure 6:
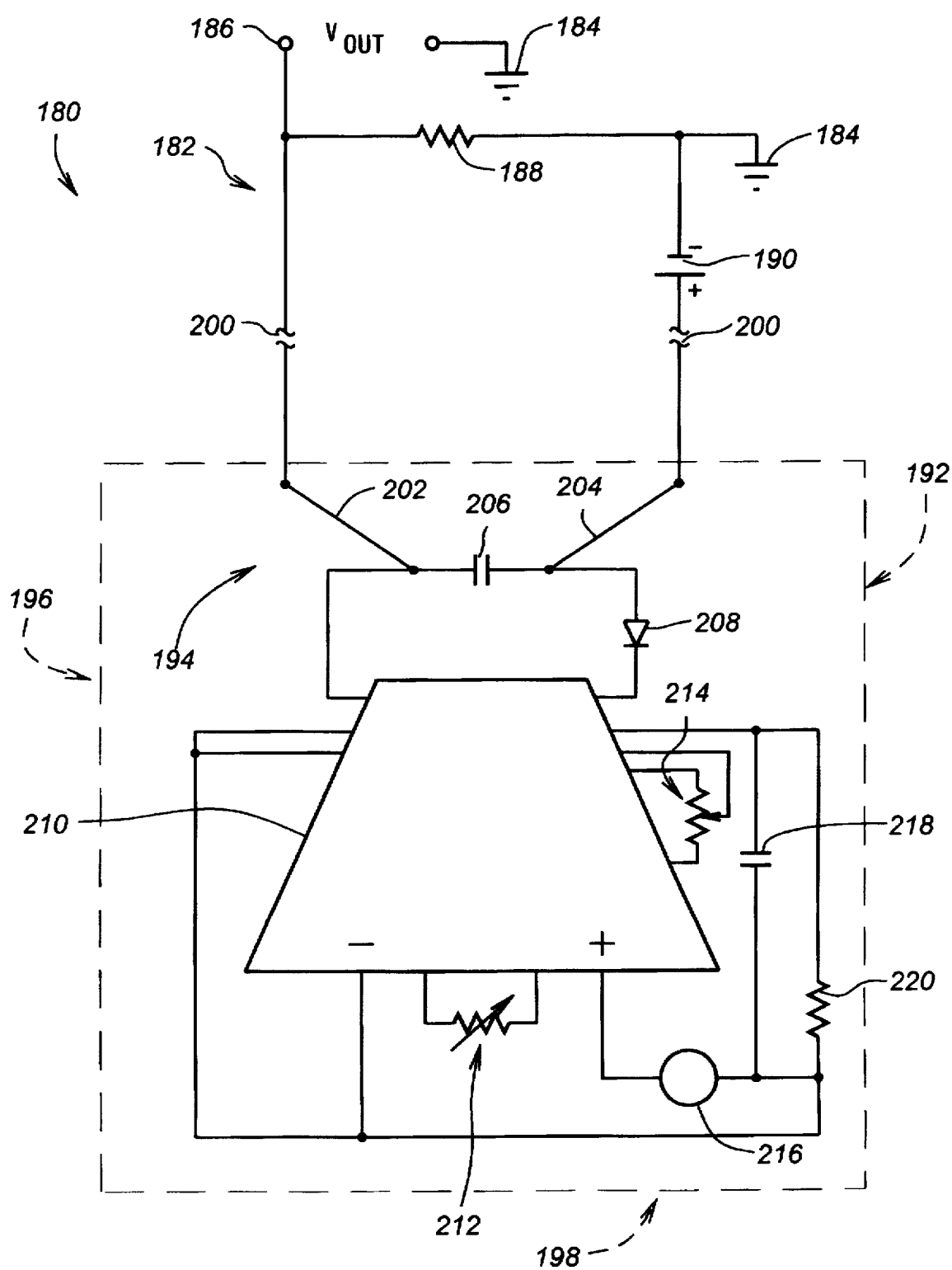
FIG. 6 is a circuit diagram of FIG. 5.

FIG. 6 shows an exemplary circuit diagram 180 according to the present invention. An external power source and external current loop receiver are shown generally as circuit 182. An output voltage, $V_{our}$ is between a ground 184 and a node 186. A resistor 188 serves as the current loop receiver and is in parallel with $V_{our}$. Resistor 188 may have a value of 1 ohm. A battery 190 serves as the power source and connects to resistor 188 and ground 184. Power source 190 may be a 24 volt d.c. battery.

Circuit 182 is electrically connectable to a data port shown as dashed line 192. Data port 192 includes an electrical interface 194 which represents the electrical connection between access port and needle electrodes, a control circuit 196, and a sensor circuit 198. Broken lines 200 indicate that circuit 182 is removably connectable to data port 192.

Interface 194 establishes the electrical connection between circuit 182 and data port 192. Two lines 202 and 204 establish this electrical connection. A capacitor 206 electrically connects to lines 202 and 204 and to a diode 208. Capacitor 206 is a 0.01 μf capacitor. Circuit 196 includes a current loop transmitter 210 having multiple pin input/output connections. Variable resistors 212 and 214 connect to transmitter 210. Circuit 198 includes a sensor 216 connected to a positive port of transmitter 210. A capacitor 218 and a resistor 220 are in parallel and connect to sensor 216.

Preferably, capacitor 218 is a 0.01 μf capacitor, and resistor 220 has a resistance of 2.5 k ohms.

Since certain changes may be made in the above-described apparatus and method without departing from the scope of the invention herein involved, all matter contained in the description or shown in the accompanying drawings shall be interpreted as illustrative and not in a limiting sense.

The invention claimed is:

1. An implantable data port, comprising:

an outer housing formed of a nonconductive, biologically compatible material and being subcutaneously implantable within a subject;

means for electrically connecting an implantable lead to said data port and for receiving an electrical signal;

a control circuit within said housing electrically connected to said means for connecting a lead;

a current loop transmitter connected to said control circuit, said current loop transmitter being adapted to produce a current proportional to said electrical signal;

a ground electrode electrically connected to said control circuit and exposed through said biologically compatible material; and at least one access port on said housing and electrically connected to said current loop transmitter for connecting said data port to a current loop receiver.

2. A system for acquiring biological data from a living organism, said system comprising:

a power source;

a data port having
an outer housing formed of a nonconductive, biologically compatible material and being subcutaneously implantable within a subject,
a control circuit with a current loop transmitter enclosed within said outer housing, and
a first electrical connection for connecting said control circuit to said power source;

an implantable sensor;

a second electrical connection connecting said sensor to said control circuit;

an electrical converter having a current loop receiver and a power source connected thereto and a third electrical connection connecting said current loop receiver to said current loop transmitter.

3. The system according to claim 2 wherein said second electrical connection comprises a lead.

4. The system according to claim 3 wherein said sensor comprises an electrode.

5. A system for acquiring biological data from a living organism, said system comprising:

a power source;

a data port having
a control circuit with a current loop transmitter, and
a first electrical connection connecting said control circuit to said power source;

a bipolar electrode;

a second electrical connection comprising a lead, said lead connecting said bipolar electrode to said control circuit;

an electrical converter having a current loop receiver and a third electrical connection connecting said current loop receiver to said current loop transmitter.

6. A system for acquiring biological data from a living organism, said system comprising:

a power source;

a data port having a control circuit with a current loop transmitter, a reference electrode, a connector connecting said reference electrode to said control circuit, and a first electrical connection connecting said control circuit to said power source;

an electrode;

a second electrical connection comprising a lead and connecting said electrode to said control circuit;

an electrical converter having a current loop receiver and a third electrical connection connecting said current loop receiver to said current loop transmitter.

7. A system for acquiring biological data from a living organism, said system comprising:

a power source;

a data port having a control circuit with a current loop transmitter, and a first electrical connection connecting said control circuit to said power source;

a female connector port in electrical communication with said control circuit;

an electrode;

a second electrical connection comprising a lead having a male connector end adapted to be received within said female connector port for connecting said electrode to said control circuit;

an electrical converter having a current loop receiver and a third electrical connection connecting said current loop receiver to said current loop transmitter.

8. A system for acquiring biological data from a living organism, said system comprising:

a power source having an electrically conductive needle;

a data port having a body of biologically compatible material;

a control circuit with a current loop transmitter, said body containing said control circuit, and a first electrical connection connecting said control circuit to said power source, said first electrical connection comprising an access port including a conductive filler, said electrically conductive needle being adapted to connect to said access port through said conductive filler;

a sensor;

a second electrical connection connecting said sensor to said control circuit;

an electrical converter having a current loop receiver and a third electrical connection connecting said current loop receiver to said current loop transmitter.

9. The system according to claim 8 wherein said third electrical connection comprises an access port including a conductive filler, and wherein said electrical converter has an electrically conductive needle for connecting to said access port.

10. A system for acquiring biological data from a living organism, said system comprising:

a power source;

a data port having a body of biologically compatible material, a control circuit with a current loop transmitter, said control circuit being contained within said body and a first electrical connection connecting said control circuit to said power source;

a sensor;

a second electrical connection connecting said sensor to said control circuit;

an electrical converter having a current loop receiver and a third electrical connection connecting said current loop receiver to said current loop transmitter, said third electrical connection comprising an access port including a conductive filler, and said electrical converter having an electrically conductive neddle for connecting to said access port.

* * * * *